United States Patent
Berkulin et al.

(10) Patent No.: US 6,753,017 B2
(45) Date of Patent: Jun. 22, 2004

(54) PROCESS FOR PREPARING DRY EXTRACTS

(75) Inventors: Wilhelm Berkulin, Andernach (DE); Karl-Hans Theissing, Alzenau (DE)

(73) Assignee: JRS Pharma LP, Patterson, NY (US)

( * ) Notice: Subject to any disclaimer, the term of this patent is extended or adjusted under 35 U.S.C. 154(b) by 0 days.

(21) Appl. No.: 09/986,116

(22) Filed: Nov. 7, 2001

(65) Prior Publication Data

US 2003/0086982 A1 May 8, 2003

(51) Int. Cl.⁷ ............................................... A61K 35/78
(52) U.S. Cl. ........................................................ 424/725
(58) Field of Search ........................................ 424/725

(56) References Cited

U.S. PATENT DOCUMENTS

| | | | |
|---|---|---|---|
| 2,756,177 A | | 7/1956 | Cannalonga et al. |
| 4,395,491 A | * | 7/1983 | Hohl et al. |
| 4,519,961 A | * | 5/1985 | Schumacher et al. |
| 4,533,674 A | | 8/1985 | Schmidt et al. |
| 5,466,452 A | | 11/1995 | Whittle |
| 5,585,115 A | | 12/1996 | Sherwood et al. |
| 5,709,880 A | | 1/1998 | Del Corral et al. |
| 5,725,883 A | | 3/1998 | Staniforth et al. |
| 5,725,884 A | | 3/1998 | Sherwood et al. |
| 5,733,578 A | | 3/1998 | Hunter et al. |
| 5,741,524 A | | 4/1998 | Staniforth et al. |
| 5,798,101 A | | 8/1998 | Haveson |
| 5,858,412 A | | 1/1999 | Staniforth et al. |
| 5,866,166 A | | 2/1999 | Staniforth et al. |
| 5,965,166 A | | 10/1999 | Hunter et al. |
| 6,030,645 A | | 2/2000 | Tritsch et al. |
| 6,103,219 A | | 8/2000 | Sherwood et al. |
| 6,106,865 A | | 8/2000 | Staniforth et al. |
| 6,153,220 A | | 11/2000 | Cummings et al. |
| 6,190,696 B1 | | 2/2001 | Groenewoud |
| 6,217,907 B1 | | 4/2001 | Hunter et al. |
| 6,217,909 B1 | | 4/2001 | Sherwood et al. |
| 6,358,533 B2 | | 3/2002 | Sherwood et al. |
| 6,383,526 B1 | | 5/2002 | Andrews et al. |
| 6,391,337 B2 | | 5/2002 | Hunter et al. |
| 6,395,303 B1 | | 5/2002 | Staniforth et al. |
| 6,447,815 B1 | * | 9/2002 | Menon et al. |
| 6,521,261 B2 | | 2/2003 | Sherwood et al. |

FOREIGN PATENT DOCUMENTS

| | | | | |
|---|---|---|---|---|
| CN | 1311016 A | | 9/2001 | |
| EP | 419308 | * | 3/1991 | |
| GB | 417552 A | | 10/1934 | |
| GB | 417552 | | 10/1934 | |
| GB | 1098065 A | | 1/1968 | |
| GB | 1098065 | | 1/1968 | |
| WO | 99 15155 A1 | | 4/1999 | ............ A61K/9/20 |

OTHER PUBLICATIONS

Editor: Budavari S.: "The Merck Index, 12ᵗʰ Edition", 1996, XP002227695, p. 1712, paragraph 10159 Merck and Co., Whitehouse Station, NJ., USA.
Database WPI Section Ch, Week 200205, Class B04, AN 2002–034992 ZP002228002 Derwent Publications Lt., London, GB.

* cited by examiner

*Primary Examiner*—Christopher R. Tate
(74) *Attorney, Agent, or Firm*—Davidson, Davidson & Kappel, LLC

(57) ABSTRACT

The process for preparing dry extracts from a liquid extract and at least one additional substance by a spray-drying process is effected by adding said at least one additional substance to the spray-drying process in a dry form during the spray-drying process.

9 Claims, No Drawings

PROCESS FOR PREPARING DRY EXTRACTS

The present invention relates to a process for preparing dry extracts.

Extracts from plants or plant parts are widely employed in the food and drug fields. In many cases, it is appropriate to dry the thus obtained extracts in order the volume of the extracts. As far as other auxiliary agents are needed for the further processing of the dry extract, these are usually admixed with the liquid extract, followed by commonly drying them. Depending on what use is intended for the thus obtained dry products, further processing steps, such as wet granulation, fluidized-bed drying, compaction etc., can follow.

It has been the object of the present invention to provide a particularly simple process for adding further substances to an extract to be dried.

According to the invention, this object is achieved by a process for preparing dry extracts from a liquid extract and at least one additional substance by a spray-drying process, wherein said at least one additional substance is added to the spray-drying process in a dry form during the spray-drying process.

The wet extract droplets formed by the spraying will mix with said at least one additional substance and are dried on their common way through the spray-dryer, The residual moisture is generally below 5%.

Surprisingly, in this way, a homogeneous free-flowing powder can be obtained, which can be used, for example, directly for tabletting. Such a product is superior to both one obtained by commonly drying a solution of the extract and auxiliary agent, and one obtained by adding the auxiliary agent to the dried extract, with respect to galenic properties, especially tabletting property. Thus, the proportion of auxiliary agent can be significantly reduced as compared to conventional processes, so that smaller tablets can be produced with the same load of active substance, or more active substance can be introduced in predetermined tablet sizes.

The process is particularly useful if the liquid extract is the extract of a medicinal plant whose extract is to be administered in the form of tablets.

Said at least one additional substance will then be a galenic auxiliary agent. Galenic auxiliary agents are known to the skilled person. There may be mentioned, for example, lactose, maltodextrin, dextrin, dry glucose, starch, microcrystalline cellulose, silicated microcrystalline cellulose, Povidone®, polyethylene glycol, calcium phosphate, magnesium stearate, precipitated silicic acid, precipitated silica, highly dispersed silica, sorbitol, mannitol, or mixtures thereof.

The particle size of the additional substance employed is of less importance. Suitable particle sizes are within a range of from 1 to 500 µm.

The process according to the invention results in adhesion of the auxiliary agents to the extracts. Therefore, the invention also relates to the dry extract thus obtained, and to a medicament containing the dry extract according to the invention.

Preferably, the medicament according to the invention is a medicament in a tablet form.

For performing the process, a usual spray-drying plant can be used in which the liquid extract is introduced into a spray tower and drying air is simultaneously fed. By spraying into a hot-air current, the liquid products are quickly and mildly dried within seconds or fractions of seconds. The liquid extract to be dried typically contains from 5 to 70% of dry substance and is introduced into the spray tower at a pressure within a range of from 10 to 150 bar through one or more high-pressure nozzles. Usually, the temperature of the fed-in drying air is between 120 and 350° C., In the process according to the invention, the dry additional substance or a mixture of such substances is also introduced into the spray tower using blow conveyance, preferably in the vicinity of the spraying nozzles for the liquid extract.

For example, the design could be as follows:

A liquid extract is provided in a storage vessel. On a second position, there are dosing scales with the additional substance employed according to the invention in a dry form. The liquid extract is sprayed in together with the finely powdered additional substance at the top of the spray tower through high-pressure nozzles using a pump. Hot air is introduced into the spray tower from below. The exhaust air leaves at the top end of the spray tower and is optionally conducted to a heat exchanger. The dried product is conducted onto a vibrating bed at the lower end of the spray tower and introduced into the further production process. Alternatively, the product may be fed into a cyclone.

EXAMPLES

Example 1

146.5 kg of St. John's wort extract having a dry content of 47.8% was spray-dried together with 30.00 kg of silicated microcrystalline cellulose at an air entry temperature of 210° C. and under a nozzle pressure of 40 bar to obtain 93.6 kg of dry product.

Example 2

5236.8 kg of St. John's wort extract having a dry content of 38% was spray-dried together with 104.6 kg of highly dispersed silica at an air entry temperature of 200° C. and under a nozzle pressure of 90 bar to obtain 2065.8 kg of dry product.

Example 3

1819.9 kg of Giant or Late Goldenrod extract having a dry content of 30% was spray-dried together with 221.7 kg of maltodextrin and 23.4 kg of highly dispersed silica at an air entry temperature of 215° C. and under a nozzle pressure of 45 bar to obtain 733.6 kg of dry product.

Example 4

1640.00 kg of valerian root extract having a dry content of 51.8% was spray-dried together with 332.00 kg of dry glucose and 48.6 kg of highly dispersed silica at an air entry temperature of 230° C. and under a nozzle pressure of 80 bar to obtain 1142.8 kg of dry product.

Example 5

658.5 kg of nettle root extract having a dry content of 32% was spray-dried together with 52.7 kg of lactose at an air entry temperature of 220° C. and under a nozzle pressure of 50 bar to obtain 262.4 kg of dry product.

What is claimed is:

1. A process for preparing a dry extract composition comprising: combining, in a spray dryer, a liquid extract of a medicinal plant and a dry substance together and spray-drying to produce a spray dried composition consisting essentially of said liquid extract and said dry substance, wherein the dry substance is selected from the group consisting of lactose, maltodextrin, dextrin, dry glucose, starch, microcrystalline cellulose, Povidone, polyethylene glycol, calcium phosphate, magnesium stearate, precipitated silicic acid, precipitated silica, highly dispersed silica, sorbitol, mannitol, and mixtures thereof.

2. The process according to claim 1, wherein the dry substance has a particle size of from 1 to 500 μm.

3. The process of claim 1, wherein the spray dried composition has a residual moisture of less than 5%.

4. The process of claim 1, wherein the liquid extract is introduced into the spray dryer via a nozzle at a pressure of from 10 to 150 bar.

5. The process of claim 1, wherein the spray dryer contains drying air having a temperature between 120 C and 350 C.

6. The process of claim 4, wherein the spray dryer contains drying air having a temperature between 120 C and 350 C.

7. The process of claim 1, wherein the dry substance is introduced into the spray dryer via a blow conveyance.

8. The process of claim 4, wherein the dry substance is introduced into the spray dryer via a blow conveyance.

9. The process of claim 6, wherein the dry substance is introduced into the spray dryer via a blow conveyance.

* * * * *